United States Patent
Van Den Berg et al.

[11] Patent Number: 5,600,142
[45] Date of Patent: Feb. 4, 1997

[54] MEASUREMENT OF VAPORIZED HYDROGEN PEROXIDE

[75] Inventors: Rian Van Den Berg, Sliedrecht, Netherlands; Mark S. Zetter, El Dorado Hills, Calif.; Keith L. Miller, El Dorado Hills, Calif.; Terry R. Todd, Placerville, Calif.

[73] Assignee: UOP, Des Plaines, Ill.

[21] Appl. No.: 451,842

[22] Filed: May 26, 1995

[51] Int. Cl.⁶ .................................................. G01N 21/35
[52] U.S. Cl. ............................... 250/339.13; 250/343
[58] Field of Search ................. 250/339.09, 339.12, 250/339.13, 343

[56] References Cited

U.S. PATENT DOCUMENTS 4,800,279  1/1989  Hieftje et al. ............... 250/339.09

FOREIGN PATENT DOCUMENTS 285251    10/1988  European Pat. Off. ........ 250/343
5-281138  10/1993  Japan ........................... 250/339.12

OTHER PUBLICATIONS

Davidson et al, "Precision of the Petrochemical Process Analysis Using N/R Spectroscopy", SPIE vol. 1681, Optically Based Methods for Process Analysis, 1992, pp. 231–235.

DiFoggio et al., "Near–Infrared Offers Benefits and Challenges in Gasoline Analysis", Oil and Gas Journal, May 1993, pp. 87–90.

*Primary Examiner*—Carolyn E. Fields
*Assistant Examiner*—Edward J. Glick
*Attorney, Agent, or Firm*—Thomas K. McBride; Eugene I. Snyder

[57] ABSTRACT

On line and essentially continuous measurements of hydrogen peroxide vapor in the presence of water vapor can be made using near infrared (NIR) spectroscopy using fiber optic cables to transmit infrared radiation between, e.g., a sterilization chamber and the NIR instrument. Hydrogen peroxide absorbs selectively at about 1420 nm, where water vapor also absorbs, but the absorbance at 1420 nm can be corrected for water vapor measurements at remote wavelengths where $H_2O_2$ is transparent. The measurement process also may be incorporated into a control system assuring optimum hydrogen peroxide vapor concentrations for the sterilization procedure.

1 Claim, 1 Drawing Sheet

MEASUREMENT OF VAPORIZED HYDROGEN PEROXIDE

This invention relates to the quantitative analysis of hydrogen peroxide in the vapor phase, whether at ambient, reduced, or elevated pressure. More particularly, this invention relates to near infrared spectroscopic analysis of vaporized hydrogen peroxide, especially as used in sterilization procedures where vaporized hydrogen peroxide must be determined in the presence of water and sometimes in the presence of diverse organic vapors.

Sterilization methods are used in a broad range of applications and have used an equally broad range of sterilization agents. By "sterilization" we refer to the complete destruction or irreversible inactivation of all microorganisms, especially on inanimate objects. The term "disinfectant" appears to be narrower in that it is directed only against organisms considered harmful. Consequently the term "sterilization" includes the use of disinfectants applied to inanimate objects. Among the traditional methods of sterilization are included heat sterilization, most commonly via steam, and chemical sterilization using a variety of agents including alcohols, aldehydes such as formaldehyde, phenols, ozone, and ethylene oxide. Chemical sterilization usually is referred to as cold sterilization for obvious reasons. Each of the methods has its own disadvantages. The major disadvantage of heat sterilization is that some objects to be sterilized can not physically withstand the necessary heat treatment, especially where the objects are polymers or delicate instruments subject to thermal degradation or damage. Various chemical sterilization agents actually react with one or more of the materials of construction of the sterilization objects, hence also must be used with caution. Chemical sterilization agents also suffer from the disadvantage that they may pose disposal or human toxicity problems, requiring extraordinary handling and/or safety procedures.

Hydrogen peroxide and peracids are powerful antimicrobial agents and effective sporicides. A 35 weight percent solution of hydrogen peroxide can be stored for prolonged periods, is easy to handle, is non-corrosive, and mixes readily with water. An important advantage of hydrogen peroxide in sterilization is that it decomposes to oxygen and water, thus presenting no disposal problems.

The use of hydrogen peroxide as a vapor in sterilization also brings along related problems and needs. As with other sterilization agents the effectiveness of hydrogen peroxide under a given set of conditions depends upon its concentration. Therefore, it is not merely important but even critical to have a rapid, accurate method for monitoring hydrogen peroxide concentration in the vapor state in order to ensure effective sterilization. Since hydrogen peroxide always is accompanied by water, a suitable measurement must be capable of selectively monitoring hydrogen peroxide concentrations in the presence of water vapor, and usually in the presence of water vapor at concentrations somewhat higher than those of hydrogen peroxide. Sterilization by hydrogen peroxide also can be performed under conditions where there is the possibility of a significant concentration of organic vapors. Therefore it is important to measure the concentration of hydrogen peroxide in the presence of organic vapors as well as to independently alert the operator to the presence of organic vapors which otherwise could invalidate the hydrogen peroxide measurements, especially by the methods described within.

Hydrogen peroxide also poses occupational health and safety issues, thus it is important to know with confidence that when sterilization is complete residual peroxide remaining after excess hydrogen peroxide decomposition is sufficiently low as to be safe. In humans, brief contact of hydrogen peroxide with the skin leads to irritation and whitening (cutaneous emphysema), the severity of which depends on concentration. Longer contact or higher concentration can lead to burns. Contact with the eyes also leads to serious injuries. Hydrogen peroxide vapor or aerosol causes irritation or damage of the upper respiratory tract and serious lung injuries. The threshold concentration for acute irritative effects of vaporized hydrogen peroxide on the respiratory tract is about 10 $mg/m^3$ in humans; the corresponding value for skin is 20 $mg/m^3$ for humans.

It also is desirable that measurements be made in real time and remotely. That is, it is desirable that the measurement process can be completed in a relatively short time, so that one can monitor the hydrogen peroxide concentration as the sterilization process proceeds. It also is desirable that measurements be done without bringing samples to the measuring instrument but instead have the measuring instrument located remotely from the sterilization chambers while monitoring $H_2O_2$ in situ. Both of the latter requisites are fulfilled using near infrared spectroscopy with optical fiber cables carrying electromagnetic radiation between the sample and the instrument with probes inserted directly into the sterilization chamber to sample hydrogen peroxide. In the context of this application a "probe" is that portion of the measuring system which brings electromagnetic radiation to the sample, which provides means for transmitting the radiation across the sample path, and which provides means for returning the transmitted radiation to the instrument for further processing. In brief, a probe contains the means necessary to cause a portion of the near infrared spectrum to be absorbed by the sample. In a variant the chamber itself can be used as a probe by mounting light senders and receivers on either side of the chamber with optical fibers carrying light to and from optical measuring instrumentation. It also is significant to note that the radiation used in the method is at such an extremely low level as to have no effect on people or products, and the method presents no fire or explosion hazard.

Our invention satisfies all of the foregoing criteria. That is, our invention accurately measures gaseous hydrogen peroxide concentrations in the presence of water vapor, measurements can be done quickly, virtually continuously, and the measuring apparatus can be located remotely vis-a-vis the sterilization chamber. In particular, the absorbance in the near infrared spectrum of hydrogen peroxide is determined at a frequency or narrow band of frequencies, and alternatively over a much broader wavelength range, where hydrogen peroxide is known to absorb in the near infrared. The concentration of water is concurrently determined from absorbance measurement at other frequencies, or via some correlation function to a total spectrum measured over a broader wavelength as stated above. Measurements may be performed in vacuo, at ambient pressure, or above ambient pressure, according to how sterilization is conducted, and even may be incorporated into a control process where the hydrogen peroxide concentration is adjusted to optimize sterilization.

SUMMARY OF THE INVENTION

The purpose of our invention is to perfect a method for analysis of hydrogen peroxide vapor in the presence of water vapor, especially under sterilization conditions. An embodiment comprises measuring absorbance in the near infrared at 1420 nanometers, measuring the absorbance in the 1350–1400, and/or 1830–2000, and/or 915–950 nanometer range to determine water concentration, subtracting from the absorbance at 1420 the contribution of water to said absorbance, and determining the concentration of hydrogen peroxide from the residual absorbance at 1420 using Beer's law. In another embodiment the presence of organic vapors is detected and measured in the 900–980 and/or 1090–1290 and/or 1550–1800 nanometer region with the absorbance at 1420 thereafter corrected for the calculated contribution from organic vapors. In yet another embodiment the near infrared spectrum is measured over a broad band of the infrared within the region of 900–2000 nanometers with analogous information obtained by applying a multivariant statistical technique to the measured spectrum in order to extract the requisite information. Other embodiments will be apparent from the ensuing description.

DESCRIPTION OF THE INVENTION

Figure 1:
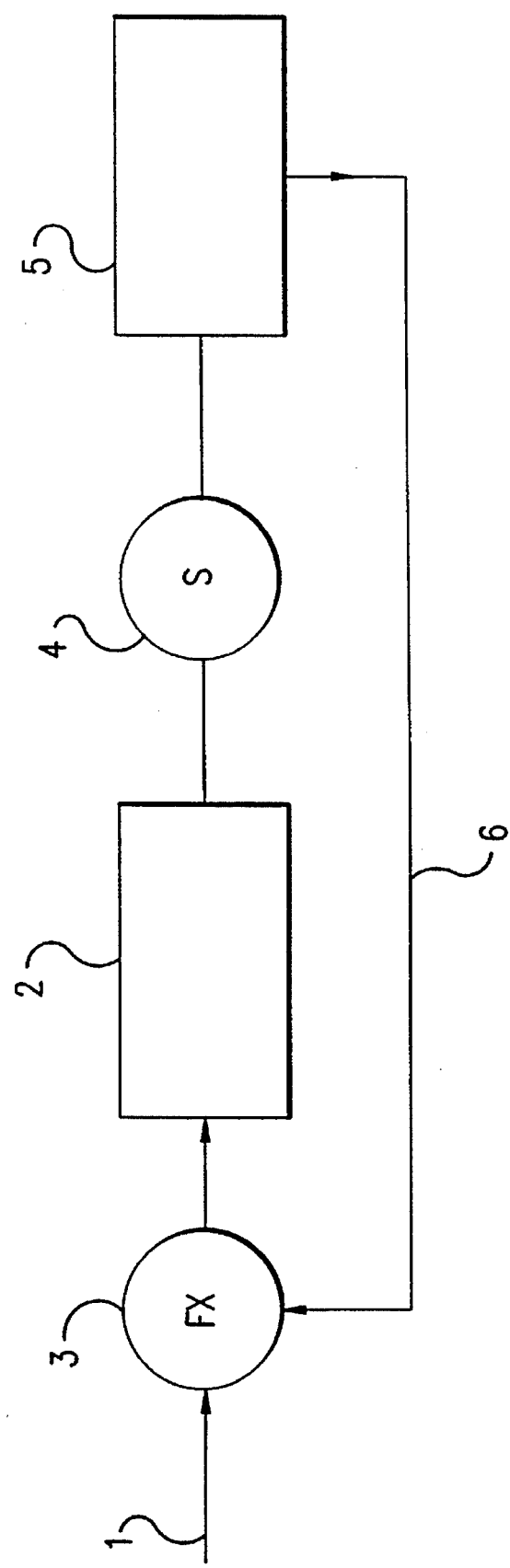
FIG. 1 illustrates a process for on-line control of the concentration of $H_2O_2$ vapors using near infrared spectroscopy as the monitoring method.

There is a need to rapidly measure hydrogen peroxide vapor concentration in the presence of water vapor, especially in real time during sterilization procedures. This need can be satisfied by the method described herein based on near infrared spectroscopy, which also has the desirable feature that instrumentation can be located remotely from the sample since the pertinent light frequencies can be transmitted readily over optical fibers. Our invention is based on the observation that hydrogen peroxide vapor has a strong absorption in the near infrared centered at approximately 1420 nanometers. The contribution to the absorbance at 1420 nm from water can be calculated by measuring the water absorbance in one or more of the 1350–1400, the 1830–2000, and 915–950 nm range where hydrogen peroxide is essentially transparent. From the known relation between water vapor absorbance in the latter two regions and its absorbance at 1420 nm one can calculate the contribution of the 1420 absorbance from water vapor to arrive at an absorbance arising solely from hydrogen peroxide. It then becomes a simple matter to apply Beer's law to calculate hydrogen peroxide concentration.

The samples which are being measured in the practice of our invention generally are gaseous samples, or head space, in sterilization chambers using hydrogen peroxide as a sterilizing agent. Since hydrogen peroxide always decomposes to form water and vapors are normally generated from aqueous hydrogen peroxide, the gaseous samples being analyzed always are at least a mixture of hydrogen peroxide and water. In addition, the samples can contain organic vapors from, e.g., outgassing, previous washes in organic solvents, and so forth, a fact which has implications both in validation of the hydrogen peroxide concentration measurements as well as in modifications of the hydrogen peroxide measurement which are elaborated upon within.

The absorbance of the vapor is measured at about 1420 nm, which is roughly the mid-point of an absorption band of hydrogen peroxide. However, since water and many organic vapors also absorb at this wavelength there is a need to correct the measured absorbance for the presence of interfering components. In general, the measured absorbance may be thought of as the sum of several absorbances, $$A_{1420}(total)=A_{1420}(H_2O_2)+A_{1420}(H_2O)+A_{1420}(organics)$$

As the foregoing clearly shows it is necessary to subtract the absorbances arising from water and organic vapors in order to correctly ascertain the absorbance associated solely with hydrogen peroxide.

The corrections associated with water absorptions may be applied by measuring the absorbance at at least one wavelength within at least one of the regions 1350–1400, 1830–2000, and 915–950 nm, regions where hydrogen peroxide is transparent (i.e., there is no absorption by hydrogen peroxide in these regions). As stated above, the absorbance must be measured at at least one wavelength in one of the foregoing regions; which region is chosen is a matter of choice. It also is possible to make more than one measurement in any or all of the foregoing regions. Additionally, one has the choice of making absorbance measurements either at one or a multiplicity of discrete wavelengths or measuring an integrated absorbance over some band of wavelengths within the stated region. Whichever variant is chosen the concentration of water then may be calculated from the measured absorbance, using the appropriate extinction coefficient at measured wavelengths where discrete absorbances are measured or using an integrated extinction coefficient where an integrated absorbance is measured. In either case one calculates the absorbance at 1420 nm arising from the concentration of water as measured in the foregoing description using the water concentration as measured above and the known extinction coefficient of water at 1420 nm. The calculated contribution of water is then subtracted from the measured absorbance at 1420 to give a corrected absorbance which, except for the possible contributions from organic vapors, represents the absorbance of hydrogen peroxide alone.

Where the absorbance of organic vapors at 1420 is small relative to the total absorbance at that wavelength, then $$A_{1420}(total)=A_{1420}(H_2O_2)+A_{1420}(H_2O)$$

Rearranging, $$A_{1420}(H_2O_2)=A_{1420}(total)-A_{1420}(H_2O)$$

It then is a simple matter to calculate the concentration of hydrogen peroxide from its absorbance using Beer's law which states A=εlc, where ε is the extinction coefficient of a substance at the measured wavelength, l is the sample path length, and c is the concentration of the substance being measured in the sample. As an example of making absorbance corrections, we have noted that the absorbance of water at 1420 nm is ca. 1/6 that of the absorbance at 1360 nm. Therefore, by measuring the absorbance at 1360 nm one can readily correct for water absorbance at 1420 nm.

It is possible to simplify the foregoing even more where the contribution of water vapor to the absorbance at 1420 nm is small, or where one needs only an approximate measurement of hydrogen peroxide concentration, by ascribing all of the absorbance at 1420 nm to hydrogen peroxide. Clearly this is inaccurate, yet for some purposes the results are adequate.

As stated above, there are possible interferences to the hydrogen peroxide measurement if other vapors are present that absorb radiation at about 1420 nm. Practically all organic materials absorb in this region, consequently organic solvent vapors generally will interfere with the measurement as described above. However, such materials also absorb in other areas of the near infrared, particularly in the regions 900–980, 1090–1290 nm, 1550–1800 nm, and 2100–2400 nm where neither hydrogen peroxide nor water absorb. Thus, if interfering organic vapors are present they can be detected, independently of hydrogen peroxide and water vapors, by measuring in these other regions either to give warning that the hydrogen peroxide measurement is not valid or to make approximate corrections to the absorbance at 1420 nm. General relationships do exist between the intensities of the organic vapor peaks in the 1090–1290 or 1550–1800 nm regions and those in the 1420 region, with a typical ratio of absorbance at any particular peak maximum to that at 1420 nm being in the range of 1.5:1 to 1:1. Thus, approximate, non-specific corrections could be made to the hydrogen peroxide value based on absorbances in non-hydrogen peroxide active regions. Of course, if the interfering substances are known more precise corrections could be made in the same manner as described for water above.

In any optical system the system reference must be established regularly, i.e., the system optical performance must be measured at regular intervals with no active sample, or other absorbing material that is subject to change, in the optical beam path. This establishes a baseline performance such that signals generated in the presence of a sample are then directly related only to the sample and not to changes in the optical system. The difficulty presented by system reference procedures for the hydrogen peroxide concentration measurements is that water vapor is generally naturally present in the optical path at a concentration comparable to that generated during hydrogen peroxide sterilization. Where measurement of water vapor itself is unimportant the aforegoing difficulty has no practical effect. However, because no reference can be easily established in ambient air, more elaborate reference procedures need to be devised where the measurement of water vapor also is required.

Where sterilization by hydrogen peroxide is performed under vacuum the first step after sealing the vacuum chamber is to evacuate it to a pressure of 20 torr or less. This removes essentially all the water vapor (740/760-ths, or 97%, is removed) and a reference spectrum can be taken, preferably automatically, after evacuation and prior to addition of hydrogen peroxide to the evacuated system.

Where sterilization is not done in vacuo, establishing a reference is somewhat more inconvenient. One method would be to insert into the entire sample path used for peroxide measurement a reference sample of a sealed tube with optical windows at each end containing dry air, or evacuated to a degree that the water vapor concentration is negligible. After the reference spectrum is obtained the reference sample is replaced and the hydrogen peroxide measurement obtained.

Other methods of establishing a reference can be envisaged. What is critical is that a reference procedure be established. However, the particular method used is not a critical part of our invention as described herein, and which method ultimately is applied is one of choice for the skilled worker.

Related to the need for periodically establishing a system reference is the need to periodically validate or calibrate the system performance. Simplistically, this is accomplished by placing in the normal sample path a calibration sample, i.e., a sample containing known concentrations of vaporized hydrogen peroxide, water, and perhaps organic vapors. If the concentrations calculated from the measured absorbances do not afford values for the analyte concentrations with sufficient accuracy, this indicates that the measuring procedure is faulty, such as may arise from faulty referencing, changing system performance, and faulty procedures. The difficulty of the foregoing procedure may be attributed to the difficulty of providing samples with accurately determined and stable concentrations of the analytes. So, for example, because of the relative instability of hydrogen peroxide it is challenging to prepare a sample with known concentrations of hydrogen peroxide vapor which do not appreciably change even over relatively short periods of time, especially in the presence of readily oxidizable organic materials.

Sterilization with hydrogen peroxide must be done at predetermined vapor levels of peroxide to be effective. Hydrogen peroxide will react with many surfaces undergoing sterilization, and also will permeate into and through plastic materials. Both of the foregoing can cause hydrogen peroxide levels in a sterilization chamber to be lower than expected leading to rapid loss of peroxide vapor. The result is an uncertain hydrogen peroxide vapor concentration with attending possibility of imperfect sterilization. Consequently there is a need of controlling hydrogen peroxide vapor concentration using in situ measurements. The foregoing NIR method of hydrogen peroxide measurement can be readily incorporated into a control process to ensure adequate vapor state concentrations throughout the sterilization procedure.

For example, if the on-line measurements are performed using an ancillary software program to make the corrections described above the program also can generate an output signal proportional to peroxide concentration to a hydrogen peroxide vapor generating device. The difference between the signal received by the hydrogen peroxide vapor generating device and a "setpoint" signal, i.e., some reference signal, then serves to generate additional hydrogen peroxide vapor until the aforementioned signal is zero. In essence the control system comprises a monitoring device (here an NIR spectrometer) with electronic output, a controller which reads the monitor electronic output and translates the difference between the actual and desired (or set-point) hydrogen peroxide vapor levels into a signal, generally an electronic signal, which is transmitted to the hydrogen peroxide generating device to produce more hydrogen peroxide.

The foregoing control process is schematically illustrated by FIG. 1. Gaseous hydrogen peroxide enters through line 1 into the sterilization chamber 2 through controller 3. The controller varies the amount of vaporized hydrogen peroxide entering 2 by, e.g., controlling the extent of vaporization from an aqueous solution of hydrogen peroxide. sensor 4 receives a signal from chamber 2 which is proportional to the vaporized hydrogen peroxide concentration and transmits it to a comparator 5, where the signal is compared to a setpoint or reference signal representing the desired hydrogen peroxide concentration. The difference between signals is translated into an electronic signal 6 transmitted by 5 to the controller 3 which determines the amount of vaporized hydrogen peroxide entering chamber 2, thereby maintaining the peroxide concentration within the chamber at the desired level.

The foregoing descriptions were couched in terms of making discrete measurements at particular wavelengths. Analogous procedures may be based upon measurements over a band of wavelengths within the region from about 900 to about 2000 nm. In particular, one may measure the near infrared spectrum of a series of samples containing known concentrations of hydrogen peroxide and water vapor in various combinations within the stated region. One then can obtain a correlation between the measured spectrum and the known concentrations of the components in the calibration sets being used by applying a multivariate statistical technique, such as partial least squares, principal component regression, and so forth. Whatever statistical technique is used effectively determines the best wavelength regions within which to make measurements and relative weights of the components of the measurement. One then can measure the near infrared spectrum of an unknown sample over the same region where the statistical correlation has been obtained and using a multivariate statistical technique applied to the measured near infrared spectrum of the unknown sample one can calculate the concentration of hydrogen peroxide vapor therein. This approach is merely an extension of the one described earlier; the difference is that statistical techniques are applied to a measured near infrared spectrum over a band of frequencies rather than using absorbances at discrete frequencies, or integrated absorbances over a narrow range of frequencies.

What is claimed is:

1. A method of determining the concentration of hydrogen peroxide vapor in the presence of water vapor in a sample containing both hydrogen peroxide and water vapors comprising:

a) measuring a first absorbance of the sample at a wavelength in a first region of approximately 1420 nanometers and at least one second absorbance at at least one wavelength selected from at least one second region of 915–950, 1350–1400 and 1830–2000 nanometers;

b) subtracting from the first absorbance the absorbance owing to water vapor as calculated from at least one second absorbance measured in the second region to afford a third absorbance at approximately 1420 nanometers corrected for water vapor; and c) determining the concentration of hydrogen peroxide vapor from said third absorbance using Beers Law.

* * * * *